(12) United States Patent
Haas et al.

(10) Patent No.: US 6,878,836 B2
(45) Date of Patent: Apr. 12, 2005

(54) PROCESS FOR THE EPOXIDATION OF PROPENE

(75) Inventors: Thomas Haas, Frankfurt (DE); Claudia Brasse, Hanau (DE); Wolfgang Wöll, Maintal-Dörnigheim (DE); Willi Hofen, Rodenbach (DE); Bernd Jaeger, Darmstadt (DE); Guido Stochniol, Haltern (DE); Norbert Ullrich, Essen (DE)

(73) Assignees: Degussa AG, Düsseldorf (DE); Uhde GmbH, Dortmund (DE)

( * ) Notice: Subject to any disclaimer, the term of this patent is extended or adjusted under 35 U.S.C. 154(b) by 0 days.

(21) Appl. No.: 10/839,572

(22) Filed: May 5, 2004

(65) Prior Publication Data

US 2004/0260102 A1 Dec. 23, 2004

Related U.S. Application Data

(60) Provisional application No. 60/486,767, filed on Jul. 11, 2003.

(30) Foreign Application Priority Data

Jun. 18, 2003 (EP) ............................................. 03013761

(51) Int. Cl.[7] .............................................. C07D 301/12
(52) U.S. Cl. ...................................... 549/531; 549/535
(58) Field of Search ................................. 549/531, 535

(56) References Cited

FOREIGN PATENT DOCUMENTS

| EP | 0 100 118 A1 | 2/1984 |
| EP | 1 190 770 A1 | 3/2002 |
| JP | 03114536 | 5/1991 |
| WO | WO 02/14297 A1 | 2/2002 |

OTHER PUBLICATIONS

Chen, L. Y. et al., "Propylene Epoxidation with Hydrogen Peroxide Catalyzed by Molecular Sieves Containing Framework Titanium," Journal of Molecular Catalysis, 1998, pp. 281–292, vol./Issue 132, Elsevier Science B.V., Amsterdam, The Netherlands.

Thiele, G. F. et al., "Propylene Epoxidation with Hydrogen Peroxide and Titanium Silicalite Catalyst: Activity, Deactivation and Regeneration of the Catalyst," Journal of Molecular Cataysis, 1997, pp. 351–356, vol./Issue 117, Elsevier Science B.V., Amsterdam, The Netherlands.

Clerici, M. G. et al., "Synthesis of Propylene Oxide from Propylene and Hydrogen Peroxide Catalyzed by Titanium Silicalite," Journal of Catalysis, 1991, pp. 159–167, vol./Issue 129, Academic Press, Inc., Duluth, Minnesota, USA.

*Primary Examiner*—Ba K. Trinh
(74) *Attorney, Agent, or Firm*—Smith, Gambrell & Russell, LLP

(57) ABSTRACT

A process for the continuous epoxidation of propene with hydrogen peroxide in the presence of a titanium silicalite catalyst and a methanol solvent, wherein the catalyst is periodically regenerated by washing with a methanol solvent at a temperature of at least 100° C. and the epoxidation reaction is carried out for periods of more than 300 h between two regeneration steps.

22 Claims, No Drawings

PROCESS FOR THE EPOXIDATION OF PROPENE

REFERENCE TO RELATED APPLICATIONS

The present application claims the benefit of U.S. Provisional Application No. 60/486,767, filed Jul. 11, 2003 and European application No. 03 013 761.6, both of which are relied on and incorporated herein by reference.

INTRODUCTION AND BACKGROUND

The invention is directed to an improved process for the continuous epoxidation of propene with hydrogen peroxide in the presence of a titanium silicalite catalyst and a methanol solvent, wherein the catalyst is periodically regenerated by washing with methanol and the epoxidation reaction is carried out for periods of more than 300 h between two regeneration steps.

PRIOR ART

The epoxidation of propene with hydrogen peroxide and a titanium silicalite catalyst is known from EP-A 0 100 118 and from M. G. Clerici, et al., Journal of Catalysis, Vol. 129, pages 159 to 167. M. G. Clerici, et al., discloses that in this reaction catalytic activity decreases with time on stream and that titanium silicalite may be regenerated by washing with solvents somewhat above reaction temperature. Suitable solvents are methanol or the solvent that is used in the reaction. It is also stated that fresh and recovered catalysts have similar activity and physical-chemical properties. However, no information is given on the deactivation behaviour of catalysts that were regenerated by washing with solvents.

JP-A 03-114 536 describes the regeneration of a titanium silicalite catalyst that was deactivated in an epoxidation reaction by washing with a solvent at a temperature that is 5 to 150° C. higher than the temperature used in the epoxidation reaction. Examples 4 and 5 disclose the regeneration of a catalyst that was used for the epoxidation of allyl chloride by washing with methanol at 70° and 85° C. No information is given on the deactivation behaviour of catalysts that were regenerated by washing with solvents.

EP-A 1 190 770 discloses a method for regenerating a titanium silicalite that has been used as an epoxidation catalyst by washing with a solvent containing a source of ammonium and/or alkali metal ions at a temperature of at least 150° C. The presence of ammonium or alkali metal ions in the washing solvent has the effect that regenerated catalysts reach high epoxide selectivities more quickly after recommencement of epoxidation. However, no information is given on the deactivation behaviour of catalysts that were regenerated by washing with a solvent. The use of a solvent containing ammonium or alkali metal ions also has the disadvantage that a recovery of the solvent from the regeneration effluents will be more difficult.

EP-A 1 190 770 also teaches that, if propene is epoxidized and the reaction temperature is raised to compensate for the deactivation of the catalyst while a constant pressure is maintained, such temperature rise will lead to a decrease in propene oxide selectivity. In order to keep the propene oxide selectivity constant the pressure has to be raised during the temperature rise in such a manner as to maintain a constant propene concentration in the reaction mixture. The epoxidation process disclosed in EP-A 1 190 770 therefore has the disadvantage that a constant product selectivity can only be achieved if the reaction mixture is permanently monitored for the propene content.

The inventors of this application have investigated the methods of regenerating titanium silicalite catalysts which have been used for the epoxidation of propene by washing them with a solvent and have investigated the use of such regenerated catalysts in the continuous epoxidation of propene for extended periods of time. During these observations, they observed the hitherto unknown effect that regenerated catalysts frequently showed a much faster loss of catalytic activity compared with the freshly prepared catalyst, although the initial activity and selectivity as well as the physical-chemical properties of the regenerated catalyst and the fresh catalyst were essentially the same.

Therefore, there was a need to improve the process for continuous epoxidation of propene with hydrogen peroxide and a titanium silicalite catalyst with a catalyst regeneration by washing with a solvent in such a way, that the regenerated catalyst can be used for a longer period of time between regeneration steps and at the same time to overcome the disadvantages known from EP-A 1 190 770.

SUBJECT OF THE INVENTION

This object is attained by a process for the continuous epoxidation of propene with hydrogen peroxide in the presence of a titanium silicalite catalyst and a methanol solvent, wherein the catalyst is periodically regenerated in a regeneration step by washing with a methanol solvent and wherein regeneration of the catalyst is carried out at a temperature of at least 100° C. and epoxidation is carried out for periods of at least 300 h between two regeneration steps.

It has been surprisingly found that the process of the invention not only permits to operate the continuous epoxidation reaction with a regenerated catalyst for a long time period, but also that high catalyst selectivity is achieved shortly after the regeneration step without the need to add sources for ammonium or alkali metal ions and that the epoxidation process can be operated at essentially constant hydrogen peroxide conversion and product selectivity by raising the reaction temperature to compensate for catalyst deactivation without the need for adjusting the reaction pressure.

DETAILED DESCRIPTION OF THE INVENTION

The invention is directed to an improved process for the continuous epoxidation of propene with hydrogen peroxide in the presence of a titanium silicalite catalyst and a methanol solvent, wherein the catalyst is periodically regenerated by washing with methanol and the epoxidation reaction is carried out for periods of more than 300 h between two regeneration steps.

For economic reasons it is preferred for an industrial scale process to use propene not in a pure form but as a technical mixture with propane that as a rule contains 1 to 15 vol. % of propane. Propene may be fed as a liquid as well as in gaseous form into the epoxidation reaction.

Hydrogen peroxide is preferably used in the form of an aqueous solution with a hydrogen peroxide content of 1 to 90 wt. %, preferably 10 to 80 wt. % and particularly preferably 30 to 70 wt. %. The hydrogen peroxide may be used in the form of a commercially available, stabilized solution. Also suitable sources of peroxide are unstabilized, aqueous hydrogen peroxide solutions such as are obtained in the anthraquinone process for producing hydrogen peroxide. Hydrogen peroxide solutions in methanol which are obtained by reacting hydrogen and oxygen in the presence of a noble metal catalyst in a methanol solvent may also be used.

Titanium silicalites are crystalline, titanium-containing zeolites preferably of the composition $(TiO_2)_x(SiO_2)_{1-x}$, where x is from 0.001 to 0.05 having a MFI or MEL crystalline structure. Such catalysts may be produced for example according to the process described in U.S. Pat. No. 4,410,501 relied on and incorporated herein by reference. The titanium silicalite catalyst is preferably employed as a shaped catalyst in the form of granules, extrudates or shaped bodies. For the forming process the catalyst may contain 1 to 99% of a binder or carrier material, all binders and carrier materials being suitable that do not react with hydrogen peroxide or with the epoxide under the reaction conditions employed for the epoxidation. Extrudates with a diameter of 1 to 5 mm are preferably used as fixed bed catalysts.

The methanol solvent used in the epoxidation reaction preferably comprises more than 90 wt. % methanol and more preferably more than 97 wt. % methanol. The methanol solvent is preferably a technical grade methanol, a solvent stream recovered in the work-up of the epoxidation reaction mixture or a mixture of both.

Hydrogen peroxide, propene and the methanol solvent may be introduced into the epoxidation reactor as independent feeds or one or more of these feeds may be mixed prior to introduction into the reactor.

In a preferred embodiment of the invention an additional base, preferably ammonia, is fed to the epoxidation reactor to control the selectivity of the catalyst. The base may be added separately or admixed to one of the above feeds to the reactor. The addition of the base may be at a constant rate. Alternatively, the base may be added to one of the feeds to the reactor in such an amount as to maintain a constant pH in the feed stream the base is added to.

In the epoxidation reaction propene is preferably employed in excess relative to the hydrogen peroxide in order to achieve a significant consumption of hydrogen peroxide, the molar ratio of propene to hydrogen peroxide preferably being chosen in the range from 1.1 to 30. The methanol solvent is preferably used in the epoxidation in a weight ratio of 0.5 to 20 relative to the amount of hydrogen peroxide solution. The amount of catalyst employed may be varied within wide limits and is preferably chosen so that a hydrogen peroxide consumption of more than 90%, preferably more than 95%, is achieved within 1 minute to 5 hours under the employed epoxidation reaction conditions.

During the epoxidation the pressure within the reactor is usually maintained at 0.5 to 5 MPa, preferably 1.5 to 3.5 MPa.

The epoxidation of propene is typically carried out at a temperature of 30 to 80° C., preferably at 40 to 60° C.

The epoxidation is preferably carried out in a fixed bed reactor by passing a mixture comprising propene, hydrogen peroxide and methanol over the catalyst fixed bed. The fixed bed reactor is preferably equipped with cooling means and cooled with a liquid cooling medium. The temperature profile within this reactor is preferably maintained such that the cooling medium temperature of the cooling means is at least 40° C. and the maximum temperature within the catalyst bed is 60° C. at the most, preferably 55° C.

When using a fixed bed reactor, the epoxidation reaction mixture is preferably passed through the catalyst bed in down flow mode, preferably with a superficial velocity from 1 to 100 m/h, more preferably 5 to 50 m/h, most preferred 5 to 30 m/h. The superficial velocity is defined as the ratio of volume flow rate/cross section of the catalyst bed. Additionally it is preferred to pass the reaction mixture through the catalyst bed with a liquid hourly space velocity (LHSV) from 1 to 20 $h^{-1}$, preferably 1.3 to 15 $h^{-1}$. It is particularly preferred to maintain the catalyst bed in a trickle bed state during the epoxidation reaction. Suitable conditions for maintaining the trickle bed state during the epoxidation reaction are disclosed in WO 02/085873 on page 8 line 23 to page 9 line 15, which is relied on and incorporated herein by reference.

In order to be able to operate the epoxidation process continuously when changing and/or regenerating the epoxidation catalyst, two or more flow reactors may if desired also be operated in parallel or in series in the before-described manner.

During the continuous oxidation of propene the titanium silicalite catalyst slowly loses catalytic activity. When the activity of the catalyst drops below the desired level the epoxidation reaction is interrupted and the catalyst is regenerated by washing with a methanol solvent at a temperature of at least 100° C. Regeneration is preferably performed at a temperature from 100 to 200° C. for a period of 0.5 to 48 hours, more preferably 2 to 24 hours and most preferably 4 to 10 hours.

When a fixed bed catalyst is used, the catalyst is preferably regenerated inside the epoxidation reactor without removing it from the reactor by passing a flow of methanol solvent through the catalyst fixed bed. Preferably the methanol solvent stream is passed through the catalyst bed in down flow mode and most preferably the flow rate is adjusted to maintain a trickle flow in the catalyst bed. Suitable conditions for maintaining a trickle flow mode are disclosed in WO 02/085873 on page 8, line 23 to page 9, line 15.

Regeneration may be performed at a constant temperature or using a temperature program. When a fixed bed catalyst is regenerated, passing the methanol solvent over the fixed bed is preferably started at the temperature used for the epoxidation reaction. The temperature is then raised to at least 100° C. and maintained at a temperature of at least 100° C. for the time necessary to carry out regeneration. Thereafter, the temperature is lowered back to the temperature used for epoxidation. Finally the methanol flow is stopped or the epoxidation is recommenced by starting to feed propene and hydrogen peroxide to the reactor. In such a temperature program, raising and lowering of the temperature is preferably performed at a rate of from 5 K/h to 30 K/h.

During regeneration with a methanol solvent the pressure is adjusted to maintain the major part of the methanol solvent in the liquid state. The necessary pressure may be attained as the autogenous vapor pressure by evaporating part of the methanol solvent or by supplying an inert gas such as nitrogen.

When a fixed bed catalyst is regenerated by passing a methanol solvent stream through the catalyst fixed bed, at least a part of the solvent that is passed through the catalyst fixed bed may be reused for regenerating the catalyst without prior purification. In a preferred embodiment of the invention, the methanol solvent is passed through the catalyst fixed bed without reuse for a period of from 2% to 30% of the time used for regeneration. Thereafter, all the methanol solvent that is passed through the catalyst fixed bed is returned to the regeneration, creating a closed loop for washing the catalyst with a methanol solvent for the remainder of regeneration time. In this embodiment of the invention the amount of methanol needed for regenerating the catalyst is considerably reduced.

The methanol solvent used for regenerating the catalyst preferably comprises more than 90% methanol and less then 10% water and more preferably more than 97 wt.-% methanol and less than 3% water. The methanol solvent is preferably a technical grade methanol, a solvent stream recovered in the work-up of the epoxidation reaction mixture or a mixture of both.

In a preferred embodiment of the invention the reaction mixture from the epoxidation reaction is worked up by a sequence comprising a depressurising step removing part of the propene, followed by a pre-separation which separates the mixture from the depressurising step into an overhead product comprising propene, propene oxide and a minor part of the methanol contained in the mixture and a bottom product comprising the major part of the methanol contained in the mixture, water and high boiling by-products. The bottom product from the pre-separation is then subjected to a hydrogenation step and the hydrogenated steam is subjected to a distillation step to give an overhead product containing more than 90 wt.-% and more preferably 97 wt.-% methanol. This overhead product is preferably used as the methanol solvent for regenerating the catalyst.

The used methanol solvent obtained from the step of regenerating the catalyst may be passed to a process stage for working up the reaction mixture of the epoxidation reaction to recover the methanol contained therein. When the preferred embodiment for working up the reaction mixture of the epoxidation reaction as described in the paragraph above is used, the methanol solvent that was used for regenerating the catalyst is preferably passed either to the hydrogenation stage or to the subsequent distillation step.

After the catalyst has been regenerated by washing with the methanol solvent the continuous epoxidation of propene is recommenced and the epoxidation is carried out for a period of at least 300 hours before the next regeneration step is performed. Preferably the epoxidation is carried out for a period of from 500 to 8000 hours between to regeneration steps, more preferably for a period of from 1000 to 4000 hours and most preferably for a period of from 1500 to 2500 hours. The ratio of the time period used for epoxidation between two regeneration steps relative to the time period of a regeneration step is preferably at least 100 and more preferably from 100 to 300.

In between two regeneration steps the epoxidation reaction is preferably operated to maintain an essentially constant hydrogen peroxide conversion. In this context, essentially constant has the meaning that hydrogen peroxide conversion varies by no more than 2% at a given reactant feed. However, if reactant feeds are changed to achieve a different production rate, hydrogen peroxide conversion may change by a larger value than 2%, but thereafter will be maintained within 2% of the new value. In order to maintain an essentially constant hydrogen peroxide conversion while the catalyst looses activity through deactivation, reaction parameters, such as temperature or pressure, have to be adjusted. In a preferred embodiment of the invention, the pressure during the epoxidation is maintained constant and the reaction temperature for the epoxidation is raised at a rate of 0.025 K/h or less to compensate for catalyst deactivation and maintain an essentially constant hydrogen peroxide conversion.

The following examples illustrate the process of the invention and the improvement over the prior art achieved by the process of the invention.

EXAMPLES

Titanium silicalite was used in the form of extrudates with 2 mm diameter shaped with silica sol as a binder as described in example 5 of EP-A 1 138 387.

$H_2O_2$ was used as a 60 wt-% solution that was prepared from an aqueous solution obtained in the extraction step of an anthraquinone process by evaporation of water without further purification. The 60 wt-% $H_2O_2$ was adjusted with 1100 ppm ammonia to a pH of 4.5 before feeding it to the epoxidation. pH values were measured with a glass electrode without correction.

Reaction products were analyzed by gas chromatography and $H_2O_2$ conversion was determined by redox titration. The catalyst $H_2O_2$ selectivity was calculated as the ratio of the amount of propene oxide formed relative to the amount of $H_2O_2$ converted.

Example 1

Comparative Example

Epoxidation of propene was carried out continuously in a tubular reactor of 300 ml volume, a diameter of 10 mm and a length of 4 m, equipped with a cooling jacket. The reactor was filled with a titanium silicalite catalyst in the form of 2 mm extrudates made with a silica sol binder according to example 5 of EP-A 1 138 387. The reactor was operated in down-flow operation mode.

The equipment furthermore comprised of three feed containers and pumps for the liquid starting materials and a liquid-gas separating vessel for collecting the reaction mixture. Reaction temperature was controlled by circulating an aqueous coolant through the cooling jacket whereby the coolant temperature was controlled by a thermostat. Reactor pressure was kept at 2.5 MPa absolute with nitrogen gas and a pressure controller.

The feed containers were charged with methanol, the 60 wt-% $H_2O_2$ solution and liquid propene. Mass flow of the feeding pumps was adjusted to result in a propene feed concentration of 43 wt-%, a methanol feed concentration of 43 wt-% and a $H_2O_2$ feed concentration of 8.4 wt-% at a total flow of 0.35 kg/h. The cooling jacket temperature was initially adjusted to 41° C. Initial $H_2O_2$ conversion was 96% at a catalyst $H_2O_2$ selectivity of 88%.

During 2500 h running time of the epoxidation process the coolant temperature was increased to 50° C. to maintain the $H_2O_2$ conversion constant at 95%. After 2500 h of operation the catalyst $H_2O_2$ selectivity had dropped to 85%. The product mixture contained 2.7 mol-% of methoxypropanols and 2.5 mol-% 1.2-propylene glycol with respect to the amount of propene oxide.

After 2500 h the reaction feed was stopped and the catalyst was regenerated by feeding to the reactor 0.35 kg/h of a 1 wt.-% aqueous hydrogen peroxide solution in down-flow mode for a period of 4 h at a temperature of 50° C.

After the regeneration procedure the feed was again changed to the reaction mixture described above and the epoxidation process was continued as described above with an initial cooling jacket temperature of 41° C. After 48 h reaction time the $H_2O_2$ conversion was 95.5% at a catalyst $H_2O_2$ selectivity of 87%. The product mixture contained 2.6 mol-% of methoxypropanols and 1.9 mol-% 1.2-propylene glycol with respect to the amount of propene oxide.

Example 2

Comparative Example

The epoxidation of propene was carried out as described in example 1.

After 2500 h the reaction feed was stopped and the catalyst was regenerated as described in EP-A 0 790 075 by feeding to the reactor 10 Nl/h nitrogen gas in down-flow mode for a period of 24 h at a temperature of 250° C.

After the regeneration procedure the epoxidation process was continued as described in example 1. After 48 h reaction time the $H_2O_2$ conversion was 95.2% at a catalyst $H_2O_2$ selectivity of 87%. The product mixture contained 2.6 mol-% of methoxypropanols and 2.1 mol-% 1.2-propylene glycol with respect to the amount of propene oxide.

Example 3

Comparative Example

The epoxidation of propene was carried out as described in example 1.

After 2500 h the reaction feed was stopped and the catalyst was regenerated by feeding to the reactor 0.35 kg/h pure methanol in down-flow mode for a period of 4 h at a temperature of 71° C.

After the regeneration procedure the epoxidation process was continued as described in example 1. After 48 h reaction time the $H_2O_2$ conversion was 93.8% at a catalyst $H_2O_2$ selectivity of 89%. The product mixture contained 2.2 mol-% of methoxypropanols and 1.0 mol-% 1.2-propylene glycol with respect to the amount of propene oxide.

After the regeneration step, the coolant temperature had to be increased to 49° C. over a period of 271 h to maintain a constant $H_2O_2$ conversion in the epoxidation process. After 271 h reaction time the $H_2O_2$ conversion was 93.9% at a catalyst $H_2O_2$ selectivity of 88%. The product mixture contained 2.5 mol-% of methoxypropanols and 1.7 mol-% 1.2-propylene glycol with respect to the amount of propene oxide.

Example 4

The epoxidation of propene was carried out as described in example 1.

After 2500 h the reaction feed was stopped and the catalyst was regenerated by feeding to the reactor 0.35 kg/h pure methanol in down-flow mode for a period of 4 h at a temperature of 150° C.

After the regeneration procedure the epoxidation process was continued as described in example 1. After 58 h reaction time the $H_2O_2$ conversion was 95.8% at a catalyst $H_2O_2$ selectivity of 90%. The product mixture contained 2.1 mol-% of methoxypropanols and 0.9 mol-% 1.2-propylene glycol with respect to the amount of propene oxide.

After the regeneration step, the coolant temperature had to be increased to 44° C. over a period of 328 h to maintain a constant $H_2O_2$ conversion in the epoxidation process. After 328 h reaction time the $H_2O_2$ conversion was 94.9% at a catalyst $H_2O_2$ selectivity of 90%. The product mixture contained 1.9 mol-% of methoxypropanols and 1.0 mol-% 1.2-propylene glycol with respect to the amount of propene oxide.

Example 4 shows that by selecting the solvent and temperature according to the invention, the time on stream of the regenerated catalyst in the epoxidation of propene can be considerably prolonged before another regeneration treatment becomes necessary. In example 4, the reaction temperature had to be raised by 3 K over a 270 h period (0.011 K/h) to compensate for the loss in catalyst activity, whereas in example 3 the temperature had to be raised by 8 K in a shorter 230 h period (0.035 K/h), indicating a reduced loss of catalyst activity over time when the epoxidation process is operated according to the invention.

The results also show, that by selecting the solvent and temperature according to the invention, a high catalyst $H_2O_2$ selectivity and low levels of by-products methoxypropanols and 1.2-propylene glycol are reached after the regeneration within a short time period of 58 h without the need for additives in the washing solvent as described in EP-A 1 190 770.

Example 4 demonstrates that in the process according to the invention a low level of by-products is maintained for a long period after the catalyst was regenerated, whereas regeneration at a lower temperature leads to increasing by-product levels when the regenerated catalyst is used over an extended period as can be seen from example 3. This proves that in the process according to the invention the regenerated catalyst shows a reduced loss of catalyst selectivity.

With the process according to the invention a high selectivity can also be maintained while the reaction temperature is raised to compensate for catalyst deactivation without the need for raising the pressure as for the process of EP-A 1 190 770. This facilitates process control because there is no need to measure the amount of propene in the liquid phase of the reaction mixture, whereas the process of EP-A 1 190 770 requires such measurement to adjust the pressure for maintaining a constant propene concentration.

Further variations and modifications of the foregoing will be apparent to those skilled n the art and are intended to be encompassed by the claims appended hereto.

We claim:

1. A process for the continuous epoxidation of propene comprising reacting propene with a source of hydrogen peroxide in the presence of a titanium silicalite catalyst and a methanol solvent, and periodically regenerating the catalyst in a regeneration step by washing with a methanol solvent, at a temperature of at least 100° C. and wherein epoxidation is carried out for periods of at least 300 h between two regeneration steps.

2. The process of claim 1, wherein epoxidation is carried out for periods of from 500 h to 8000 h between two regeneration steps.

3. The process of claim 1 or claim 2, wherein after regeneration of the catalyst the reaction temperature for the epoxidation is raised by 0.025 K/h or less to compensate for catalyst deactivation and to maintain an essentially constant hydrogen peroxide conversion.

4. The process of claim 1 or claim 2, wherein the catalyst is regenerated at a temperature from 100° C. to 200° C. for a period of 0.5 to 48 hours.

5. The process of claim 1 or claim 2, wherein the ratio of the period of epoxidation between two regeneration steps relative to the period of regeneration is at least 100.

6. The process of claim 1 or claim 2, wherein the epoxidation is performed in a catalyst fixed bed by passing a mixture comprising propene, a source of hydrogen peroxide and methanol over the catalyst fixed bed.

7. The process of claim 6, further comprising regenerating the catalyst by passing said methanol solvent as a stream through the catalyst fixed bed and reusing at least a part of the methanol solvent that has passed through the catalyst fixed bed for regenerating the catalyst without prior purification.

8. The process of claim 6, wherein the methanol solvent is passed over the catalyst fixed bed in down-flow mode.

9. The process of claim 7, wherein the methanol solvent is passed over the catalyst fixed bed in down-flow mode.

10. The process of claim 6, wherein the flow of the methanol solvent is maintained in a trickle-flow mode.

11. The process of claim 7, wherein the flow of the methanol solvent is maintained in a trickle-flow mode.

12. The process of claim 8, wherein the flow of the methanol solvent is maintained in a trickle-flow mode.

13. The process of claim 1, wherein the catalyst is regenerated with a methanol solvent stream obtained from working up the reaction mixture of the epoxidation.

14. The process of claim 1, wherein the methanol solvent that was used for regenerating the catalyst is passed to a process stage for working up reaction mixture of the epoxidation.

15. A process for the continuous epoxidation of propene to form propene oxide comprising forming an epoxidation reaction mixture of propene with a source of hydrogen peroxide in the presence of a sufficient amount of a titanium silicalite epoxidation catalyst and a methanol solvent, carrying out an epoxidation reaction with said reaction mixture for periods of at least 300 h between two regeneration steps, and periodically regenerating said catalyst in a regeneration step by washing said catalyst with a methanol solvent, said regeneration of the catalyst being carried out at a temperature of at least 100° C.

16. The process of claim 15, wherein the source of hydrogen peroxide is an aqueous solution containing 1 to 90 wt. % of hydrogen peroxide.

17. The process of claim 15, wherein the catalyst is a titanium containing zeolite of the formula $(TiO_2)_x(SiO_2)_{1-x}$ where x is 0.001 to 0.05 and having a MFI or MEL crystalline structure.

18. The process of claim 15, wherein a source of ammonia is added to the reaction mixture.

19. The process of claim 15, wherein the methanol used for regeneration is passed through the catalyst in down flow mode with a flow rate to maintain a trickle flow in the catalyst.

20. The process of claim 15, wherein the epoxidation catalyst is in a fixed bed and epoxidation is performed by passing a mixture comprising propene, hydrogen peroxide and methanol over the catalyst fixed bed with cooling if necessary to maintain the temperature of the fixed bed not higher than 60° C.

21. The process of claim 15, wherein the temperature of the reaction mixture is lowered back to a reaction temperature below 100° C. after the catalyst is regenerated by passing a methanol solvent stream through the catalyst.

22. The process of claim 21, wherein the reactive temperature is raised or lowered for the regeneration step by 5 k/h to 30 k/h.

* * * * *